United States Patent
McGeer et al.

(10) Patent No.: US 10,653,651 B2
(45) Date of Patent: *May 19, 2020

(54) KIT FOR TREATING CANCER WITH LOW MOLECULAR WEIGHT COMPONENTS OF AURIN TRICARBOXYLIC ACID COMPLEX

(71) Applicant: Aurin Biotech Inc., Vancouver (CA)

(72) Inventors: Patrick McGeer, Vancouver (CA); Moonhee Lee, Vancouver (CA)

(73) Assignee: Aurin Biotech Inc., Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/533,613

(22) Filed: Aug. 6, 2019

(65) Prior Publication Data

US 2020/0009096 A1     Jan. 9, 2020

Related U.S. Application Data

(60) Continuation of application No. 15/990,736, filed on May 28, 2018, now Pat. No. 10,398,666, which is a division of application No. 14/686,620, filed on Apr. 14, 2015, now Pat. No. 10,004,707.

(60) Provisional application No. 61/979,699, filed on Apr. 15, 2014.

(51) Int. Cl.
*A61K 31/194* (2006.01)
*A61K 45/06* (2006.01)

(52) U.S. Cl.
CPC ............ *A61K 31/194* (2013.01); *A61K 45/06* (2013.01)

(58) Field of Classification Search
CPC .................. A61K 31/194; A61K 45/06
See application file for complete search history.

(56) References Cited

U.S. PATENT DOCUMENTS

| | | | |
|---|---|---|---|
| 4,007,270 A | 2/1977 | Bernstein | |
| 4,880,788 A | 11/1989 | Moake | |
| 5,434,185 A | 7/1995 | Collins et al. | |
| 6,538,028 B1 | 3/2003 | Pierson, III et al. | |

OTHER PUBLICATIONS

Cushman, M., et al., "Structural investigation and anti-HIV activities of high molecular weight ATA polymers", J Org Chem, 1992, 57(26):7241-7248.
Gonzalez, R.G., et al., "Fractionation and structural elucidation of the active components of aurintricarboxylic acid, a potent inhibition of protein nucleic acid interactions", Biochimica et Biophysica Acta, 1979, 562:534-545.
Neidle, S., ed., "Cancer Drug Design and Discovery", Elsevier/Academic Press, 2008, pp. 427-431.
Fraifeld et al., Abstract, Anticancer Research, 200, 21(3B), 1975-1978.
Wang et al., "Ovarian cancer, the coagulation pathway, and inflammation", Journal of translational medicine, 2005, 3, 1-20.

(Continued)

Primary Examiner — Savitha M Rao

(57) ABSTRACT

A method of preventing and/or treating cancer in a subject is provided. The method includes administering to the subject a composition comprising an effective amount of an active agent selected from the group consisting of aurin tricarboxylic acid (ATA), aurin quadracarboxylic acid (AQA), aurin hexacarboxylic acid (AHA), aurin tricarboxylic acid complex (ATAC), and pharmaceutically acceptable salts thereof. The method excludes administration of components of crude aurin tricarboxylic acid greater than or equal to 1 kilodalton in molecular weight.

7 Claims, 11 Drawing Sheets

(56) References Cited

OTHER PUBLICATIONS

Dinda et al. "Inhibition of proliferation of T47D human breast cancer cells: Alterations in progesterone receptor and p53 tumor suppressor protein", Molecular and cellular biochemistry 175, 1997, pp. 81-89.
Toi et al., "Tumor angiogenesis in breast cancer: Its importance as a prognostic indicator and the association with vascular endothelial growth factor expression", Breast cancer research and treatment 36, 1995, pp. 193-204.
Hallock et al., "Aurintricarboxylic Acid Inhibits Protein Synthesis Independent, Sanguinarine-Induced Apoptosis and Oncosis", Toxicologic Pathology, 35:300-309, 2007.
Aurintricarboxylic acid inhibits endothelial activation, complement activation, and von Willebrand factor secretion in vitro and attenuates hyperacute rejection in an ex vivo model of pig-to-human pulmonary xenotransplantation; Hyun Kyung Kim; Ji-Eun Kim; Hyun Cho Wi; Sang Woo Lee; Ji Yeon Kim; Hee Jung Kang; Young Tae Kim; Xenotransplantation: 2008, vol. 15, Issue 4, pp. 246-256.
Hyperacute lung rejection in the pig-to-human model platelet receptor inhibitors synergistically modulate complement activation and lung injury; Pfeiffer, Steffe; Zorn, George L. III; Zhang, Jian-Ping; Giorgio, Todd D.; Robson, Simon C.; Azimzadeh, Agnes M.; Pierson, Richard N. III; Transplantation: 2003—vol. 75, Issue 7, p. 953-959.

KIT FOR TREATING CANCER WITH LOW MOLECULAR WEIGHT COMPONENTS OF AURIN TRICARBOXYLIC ACID COMPLEX

RELATED APPLICATION

This application is a continuation of U.S. application Ser. No. 15/990,736 filed 28 May 2018, pending, which is a divisional of application Ser. No. 14/686,620, filed 14 Apr. 2015, now U.S. Pat. No. 10,004,707, issued 26 Jun. 2018, which claims the benefit of the filing date of U.S. Provisional Application No. 61/979,699 filed 15 Apr. 2014. The disclosure of each of the previously referenced U.S. patent applications and patents (if applicable) is hereby incorporated by reference in its entirety.

TECHNICAL FIELD

The present invention pertains to methods and kits for prevention and treatment of various types of cancer.

BACKGROUND

Effective methods and kits for preventing and treating various types of cancer are urgently needed.

SUMMARY

One aspect of the invention provides a method of preventing and/or treating cancer in a subject comprising administering to the subject a composition comprising an effective amount of an active agent selected from the group consisting of aurin tricarboxylic acid (ATA), aurin quadracarboxylic acid (AQA), aurin hexacarboxylic acid (AHA), aurin tricarboxylic acid complex (ATAC), and pharmaceutically acceptable salts thereof, wherein the active agent excludes components greater than or equal to 1 kilodalton in molecular weight.

The active agent of the method may be ATA, AQA, AHA, or ATAC. ATAC may comprise a mixture of two or more of ATA, AQA and AHA. ATAC may comprise 50 to 90% ATA, 10 to 30% AQA, and 1 to 20% AHA.

The cancer being treated by the method may be glioblastoma, pancreatic cancer, lung cancer, breast cancer, B-cell carcinoma, chronic myelogenous leukemia, colorectal cancer, or bone osteosarcoma. The cancer may be characterized by growth which is enhanced by complement activation and which is inhibited by ATA, AQA, AHA and/or ATAC. The cancer may be characterized by enhanced expression of Factor H, VEGF, or both, and which is inhibited by ATA, AQA, AHA and/or ATAC. Apoptosis of cancer cells may be stimulated by ATA, AQA, AHA and/or ATAC. Release of lactic dehydrogenase by cancer cells may be stimulated by ATA, AQA, AHA or ATAC.

The method may exclude co-administration of any other active agent. The method may further comprise co-administering an anti-cancer agent.

Another aspect of the invention provides a kit comprising an active agent selected from the group consisting of ATA, AQA, AHA, ATAC, and a pharmaceutically acceptable salt thereof, and a package insert comprising instructions for using the active agent to treat cancer in a subject, wherein the active agent excludes any components greater than or equal to 1 kilodalton in molecular weight.

The cancer being treated by the kit may be glioblastoma, pancreatic cancer, lung cancer, breast cancer, B-cell carcinoma, chronic myelogenous leukemia, colorectal cancer, or bone osteosarcoma. The cancer may be characterized by growth which is enhanced by complement activation and which is inhibited by ATA, AQA, AHA and/or ATAC. The cancer may be characterized by enhanced expression of Factor H, VEGF, or both, and which is inhibited by ATA, AQA, AHA and/or ATAC. Apoptosis of cancer cells may be stimulated by ATA, AQA, AHA and/or ATAC. Release of lactic dehydrogenase by cancer cells may be stimulated by ATA, AQA, AHA or ATAC.

The foregoing discussion merely summarizes certain claims of the inventions and is not intended, nor should it be construed, as limiting the inventions in any way.

BRIEF DESCRIPTION OF DRAWINGS

In drawings which show non-limiting embodiments of the invention.

DETAILED DESCRIPTION

Figure 1A:
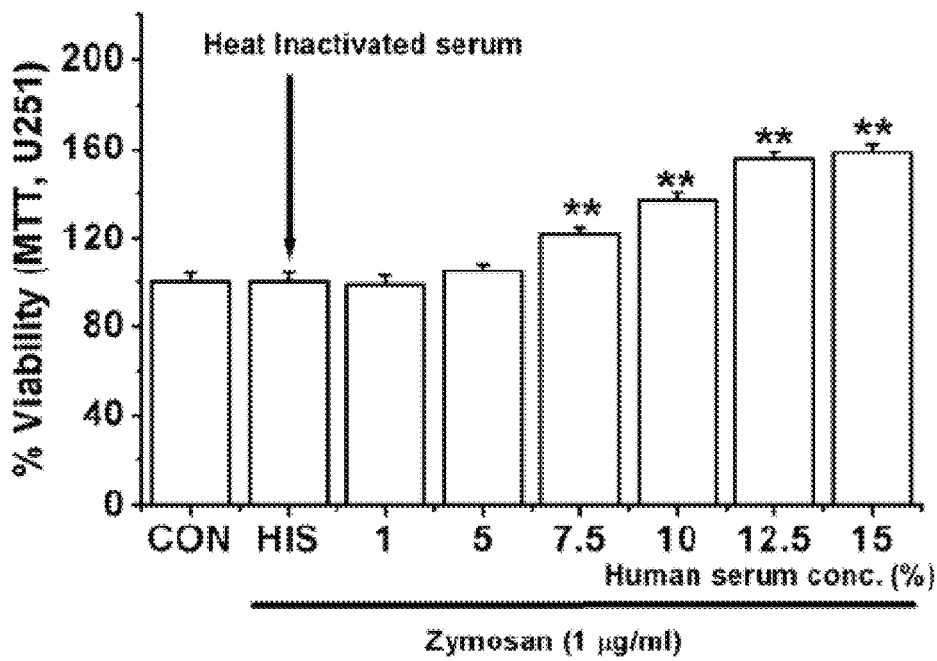
FIG. 1(a) is a graph plotting U251 malignant glioblastoma human cell viability as a function of zymosan-activated human serum concentration.

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than in a restrictive, sense.

The term "anti-cancer agent" as used herein refers to any compound (including its derivatives) which may be used to treat cancer and which is used in combination with one or more of the active agents according to the cancer treatment methods of the present invention. Anti-cancer agents for use in the present invention include, for example, aldesleukin; alemtuzumab; alitretinoin; allopurinol; altretamine; amifostine; anastrozole; arsenic trioxide; asparaginase; bevacizumab; bexarotene; bleomycin; busulfan; calusterone; capecitabine; carboplatin; carmustine; celecoxib; chlorambucil; cisplatin; cladribine; cyclophosphamide; cytarabine; dacarbazine; dactinomycin; actinomycin D; darbepoetin alfa; daunorubicin, daunomycin; denileukin diftitox, dexrazoxane; docetaxel; doxorubicin; dromostanolone propionate; Elliott's B Solution; epirubicin; Epoetin alfa estramustine; etoposide phosphate; etoposide; exemestane; Filgrastim; floxuridine; fludarabine; fluorouracil; fulvestrant; gemtuzumab ozogamicin; gleevec; goserelin acetate; hydroxyurea; ibritumomab tiuxetan; idarubicin; ifosfamide; imatinib mesylate; interferon alfa-2a; interferon alfa-2b; irinotecan;

letrozole; leucovorin; levamisole; lomustine; meclorethamine; megestrol acetate; melphalan; mercaptopurine; mesna; methotrexate; methoxsalen; mitomycin C; mitotane; mitoxantrone; nandrolone phenpropionate; nofetumomab; oprelvekin; oxaliplatin; paclitaxel; pamidronate; pegademase; pegaspargase; pegfilgrastim; pentostatin; pipobroman; plicamycin: mithramycin; porfimer sodium; procarbazine; quinacrine; ramucirumab; rasburicase; rituximab; sargramostim; streptozocin; surafenib; talbuvidine; talc; tamoxifen; tarceva; temozolomide; teniposide; testolactone; thioguanine; thiotepa; topotecan; toremifene; tositumomab; trastuzumab; tretinoin; uracil mustard; valrubicin; valtorcitabine; vinblastine; vinorelbine; zoledronate; and mixtures thereof, among others.

The term "cancer" as used herein refers to the physiological condition in mammals that is typically characterized by unregulated cell growth. The term "cancer" includes cancer of any origin, including benign and malignant cancers, metastatic and non-metastatic cancers, and primary and secondary cancers. The term "cancer" includes reference to cancer cells. Examples of cancers include, but are not limited to, cancers of the bladder, blood, bone, brain/CNS, breast, cervix, colon, duodenum, esophagus, eye, gall bladder, heart, kidney, larynx, liver, lung, mouth, ovary, pancreas, pharynx, prostate, rectum, stomach, testis, uterus, as well as AIDS-related cancers, Hodgkin's disease, non-Hodgkin's lymphoma, multiple myeloma, melanoma, leukemia (including lymphocytic leukemia, hairy cell leukemia, and acute myelogenous leukemia), choriocarcinoma, rhabdomyosarcoma, and neuroblastoma.

The term an "effective amount" as used herein refers to the amount of active agent sufficient to elicit a desired biological response or, equivalently, to inhibit an undesired biological response. An amount of a particular active agent that is effective may vary depending on such factors as the desired biological response, severity of the disease, the activity of the active agent to be delivered, the route of administration, the rate of excretion of the active agent being employed, the duration of the treatment, other drugs, compounds or materials used in combination with the particular active agent employed, the subject's age, sex, weight, condition, general health and prior medical history of the subject, and like factors well known in the medical arts. In general, an "effective amount" will be that amount of the active agent that is the lowest dose effective to produce the desired biological response. Such an "effective amount" will generally depend upon the factors described above. Generally, an "effective amount" will range from about 2 to about 200 mg per kilogram of body weight per day, more preferably from about 10 to about 50 mg per kg per day. If desired, daily dosage in an "effective amount" may be administered as one dose, or two, three, four, five, six or more sub-doses administered separately at appropriate intervals throughout the day, optionally, in unit dosage forms.

The term a "package insert" as used herein refers to instructions customarily included in commercial packages of medicaments that contain information about the indications, usage, dosage, administration, contraindications, other medicaments to be combined with the packaged product, and/or warnings concerning the use of such medicaments, and the like.

The term "pharmaceutically acceptable carrier" as used herein refers to one or more excipients, stabilizers, fillers, binders, humectants, disintegrating agents, solution retarding agents, absorption accelerators, wetting agents, absorbents, lubricants, coloring agents, diluents, emulsifiers, preservatives, solubilizing agents, suspending agents and the like that are suitable for use with the subject being exposed thereto at the dosages and concentrations employed without undue adverse side effects (such as toxicity, irritation, and allergic response) commensurate with a reasonable benefit/risk ratio. Examples of pharmaceutically acceptable carriers include water, citrate or phosphate buffers, starches, lactose, sucrose, glucose, mannitol, carboxymethylcellulose, alginates, gelatin, polyvinyl pyrrolidone, glycerol, agar, calcium carbonate, alginic acid, sodium carbonate, paraffin, quaternary ammonium compounds, cetyl alcohol, glycerol monostearate, kaolin and bentonite clay, talc, calcium stearate, magnesium stearate, polyethylene glycols, sodium lauryl sulfate, ethyl alcohol, isopropyl alcohol, ethyl carbonate, ethyl acetate, benzyl alcohol, benzyl benzoate, propylene glycol, 1,3-butylene glycol, oils, tetrahydrofuryl alcohol, fatty acid esters, thioxylated isostearyl alcohols, polyoxyethylene sorbitol and sorbitan esters, microcrystalline cellulose, aluminum metahydroxide, and tragacanth, and mixtures thereof and other ingredients that are well known to those skilled in the art.

The term "pharmaceutically acceptable salt" as used herein, refers to toxicologically compatible organic or inorganic salts of the active agent. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, alkali metal (e.g., sodium and potassium) salts, alkaline earth metal (e.g., magnesium) salts, and ammonium salts. A pharmaceutically acceptable salt can have one or more charged atoms and/or one or more counter ion. If the active agent is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. If the active agent is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The terms "prevent", "preventing", "prevention" and "preventative" as used herein refers to arrest, delay of onset (i.e., the period prior to clinical manifestation of a disease) and/or reduction of the risk of developing or worsening a disease in a subject.

The term "subject" as used herein, refers to an individual to whom an active agent is to be delivered, e.g., for preventative and/or treatment purposes. The term "subject" includes mammals, in particular humans and domesticated mammals.

The terms "treat", "treating" and "treatment" as used herein refers to an approach for obtaining desired clinical results. Desired clinical results can include, but are not limited to, reduction or alleviation of at least one symptom of a disease.

For example, treatment can be diminishment of at least one symptom of disease, diminishment of extent of disease, stabilization of disease state, prevention of spread of disease, delay or slowing of disease progression, palliation of disease, diminishment of disease reoccurrence, remission of disease, prolonging survival with disease, or complete eradication of disease.

Aspects relate to methods of preventing and/or treating cancer by administration to a subject of an effective amount of aurin tricarboxylic acid (ATA), aurin quadracarboxylic acid (AQA), aurin hexacarboxylic acid (AHA), or aurin tricarboxylic acid complex (ATAC).

ATA has an approximate molecular weight of 422.
AQA has an approximate molecular weight of 573.
AHA has an approximate molecular weight of 857.
ATAC is a mixture of two or more of ATA, AQA and AHA.

ATA, AQA, and AHA are distinct low molecular weight components of the complex mixture of compounds produced by the published methods of synthesis of aurin tricarboxylic acid. These low molecular weight components are to be distinguished from the content of so-called aurin tricarboxylic acid described by such published synthetic methods as well as from the content of any commercially available material described as aurin tricarboxylic acid. Since the synthetic and commercial products have never been shown to contain aurin tricarboxylic acid as the only, or even a major, constituent of such products, they are described herein as "crude aurin tricarboxylic acid". Crude aurin tricarboxylic acid was described and used for example in U.S. Pat. No. 4,007,270 to Bernstein et al. and U.S. Pat. No. 4,880,788 to Moake et al. Crude aurin tricarboxylic acid is comprised mostly of high molecular weight components greater than 1 kDa as explained for example by Gonzales et al. (1979). "Fractionation and structural elucidation of the active components of aurin tricarboxylic acid, a potent inhibitor of protein nucleic acid interactions." *Biochim Biophys Acta* 563,534-545. Moreover, as described by Cushman M et al. 1992, "Structural investigation and anti-HIV activities of high molecular weight ATA polymers." *J Org Chem* 57: 7241-8, the properties of these high molecular weight constituents are completely different from the properties of ATA, AQA, AHA, and ATAC as revealed in this invention.

ATA, AQA, AHA and ATAC can for example be derived in small amounts by passing crude aurin tricarboxylic acid through a 1 kDa filter.

In some embodiments ATAC comprises or consists of a mixture of two or more of ATA, AQA and AHA. In some embodiments for example, ATAC may comprise or consist of 50 to 90% ATA, 10 to 30% AQA, and 1 to 20% AHA.

ATA, AQA, AHA and ATAC are individually and collectively referred to herein as "low molecular weight components of crude ATA".

Without being bound by any particular theory, one mechanism by which administration of low molecular weight components of crude ATA may prevent and/or treat cancer is through inhibition of complement activation which is used by cancer cells to stimulate their own growth while attacking surrounding normal cells. Cancer cells may have enhanced protection from complement attack compared with surrounding normal cells by expressing elevated levels of such self-protective proteins as Factor H, protectin (CD 59), decay accelerating factor (CD 55), and possibly others. Cancer cells may also enhance their survival by generating and releasing vascular endothelial growth factor (VEGF) to provide themselves with a necessary blood supply. Low molecular weight components of crude ATA may prevent and/or treat cancer through inhibiting cancer cell expression of one or more self-protective proteins and/or VEGF. Low molecular weight components of crude ATA may also prevent and/or treat cancer through inducing cancer cell apoptosis. Regardless of the mechanism, embodiments provide for the administration of ATA, AQA, AHA and ATAC to prevent cancer in subjects at risk for cancer and to treat cancer in subjects afflicted with cancer.

In some embodiments, ATA, AQA, AHA and/or ATAC may be the only active agents that is/are administered. In other embodiments, they may be co-administered with one or more other active agents, such as one or more anti-cancer agents.

In some embodiments, compositions comprising ATA, AQA, AHA and ATAC may be presented in unit dosage form. The amounts of ATA, AQA, AHA and ATAC that can be combined with a pharmaceutically acceptable carrier to produce a single dosage form will generally be the amount that produces a therapeutic effect. In some embodiments, out of one hundred percent, this amount will range from about 1 percent to about 99 percent of active agent, from about 5 percent to about 70 percent of active agent, or from about 10 percent to about 30 percent of active agent.

While it is possible for ATA, AQA, AHA and/or ATAC to be administered alone, it may be preferable to administer them in combination with one or more pharmaceutically acceptable carriers as a composition.

In some embodiments, the administration route of ATA, AQA, AHA and ATAC, alone or in a composition, in terms of effect may be local or systemic (enteral or parenteral), and in terms of location may for example be buccal, epicutaneous, epidural, intraarticular, intracardiac, intracavernous, intracerebral, intracerebroventricular, intradermal, intramuscular, intraosseous, intraperitoneal, intrathecal, intrauterine, intravaginal, intravenous, intravesical, intravitreal, nasal, oral, rectal, subcutaneous, sublingual, sublabial, transdermal, transmucosal, and the like.

In some embodiments, oral administration may be in the form of capsules, cachets, pills, tablets, lozenges, pastes, powders, granules, or as a solution or a suspension in an aqueous or non-aqueous liquid, or as an oil-in-water or water-in-oil liquid emulsion, or as an elixir or syrup, or as pastilles or as mouth washes and the like. In some embodiments, compositions in solid dosage forms for oral administration include capsules, tablets, pills, dragees, powders, granules and the like. The solid dosage forms may be scored or prepared with coatings and shells, such as enteric coatings and other coatings. They may also be formulated so as to provide slow or controlled release of ATA, AQA, AHA and ATAC. In some embodiments, compositions in liquid dosage forms for oral administration include emulsions, microemulsions, solutions, suspensions, syrups and elixirs. In some embodiments, topical or transdermal administration may be in the form of powders, sprays, ointments, pastes, creams, lotions, gels, solutions, controlled-release patches and inhalants. In some embodiments, parenteral administration (e.g. intravenous administration) may be in the form of solutions in physiologically compatible buffers.

Regardless of the route of administration selected, in some embodiments ATA, AQA, AHA and ATAC are formulated into pharmaceutically acceptable dosage forms by conventional methods.

Aspects relate to a kit comprising ATA, AQA, AHA and/or ATAC, and a package insert comprising instructions for using ATA, AQA, AHA and/or ATAC to prevent or treat cancer in a subject.

EXAMPLES

The invention can be further understood by reference to the following examples, which are provided by way of illustration and are not meant to be limiting.

Example 1

Efficacy of ATA, AHA, AQA and ATAC against brain cancer was tested using the U251 malignant glioblastoma human cell line.

To obtain normal serum, blood samples from healthy individuals were treated at 37° C. for 3 h to promote clotting. Samples were then centrifuged at 3,000 g for 10 min and the clear serum was harvested.

The ATAC used comprised approximately 78% ATA, 15% AQA, and 7% AHA. In addition, ATA, AQA and AHA that had been separated by size exclusion chromatography were also tested individually, their purity having been verified by mass spectrometry.

U251 cells were grown in DMEM medium containing 10% fetal bovine serum (FBS), 100 IU/mL penicillin, and 100 µg/mL streptomycin (Invitrogen™, Carlsbad, Ca.) under humidified 5% $CO_2$ and 95% air until confluence was reached. This usually required 3 days of incubation. Aliquots of these cells (~2×$10^5$ cells) were added to 24-well plates.

Experiment 1 was designed to determine the effect of ATA, AHA, AQA and ATAC on U251 cell growth in the presence of complement activated human serum. In Experiment 1(a), U251 cells were treated with various concentrations of human serum (1, 5, 7.5, 10, 12.5, 15%) in DMEM and incubated with 1 µg/mL zymosan at 37° C. for 72 h. Control U251 cells (CON) were incubated in fresh DMEM only. As a further control U251 cells were treated with 10% human serum heated at 56° C. for 30 min to heat inactivate complement (HIS) before incubation with 1 µg/ml zymosan. In Experiment 1(b), U251 cells were treated with various concentrations of ATAC, ATA, AQA and AHA (0.1, 1, 5, 10, 30, 50 µM) in DMEM with 15% human serum and incubated with 1 µg/mL zymosan at 37 ° C. for 72 h. In both Experiments 1(a) and 1(b), following incubation, cell viability was evaluated by MTT (3-[4,5-dimethylthiazol-2-yl]-2,5 diphenyl tetrazolium bromide) assays by adding MTT to the cell cultures to reach a final concentration of 1 mg/mL. Following a 1 h incubation at 37° C., the dark crystals formed were dissolved by adding a SDS/DMF extraction buffer (300 µL, 20% sodium dodecyl sulfate, 50% N,N-dimethylformamide, pH 4.7). Plates were subsequently incubated overnight at 37° C. and optical densities at 570 nm were measured by transferring 100 µL aliquots to 96-well plates and using a plate reader with a corresponding filter.

Experiment 2 was designed to determine the effect of ATA, AQA, and AHA on the expression and release of Factor H and VEGF by U251 cells. Cells were grown in DMEM for 24 h at 37° C., after which ATA, AQA, or AHA was added to the medium at a final concentration of 10 µM and incubation carried out for a further 24 h. The medium was drawn off, and the cells washed with PBS. Lysis buffer was then added to the cells. Forty microliters of the cell lysate, or the supernatant media, were loaded onto 12% polyacrylamide gels and separated under non-reducing conditions (70 V, 3-6 h). Following SDS-PAGE, proteins were transferred to a PVDF membrane (Bio-Rad™, CA) at 30 mA for 2 h. The membranes were blocked with 5% milk in PBS-T (80 mM $Na_2HPO_4$, 20 mM $NaH_2PO_4$, 100 mM NaCl, 0.1% Tween 20, pH 7.4) for 1 h, and incubated overnight at 4° C. with primary antibodies for Factor H (Cytotech™, goat 1/1000) and for VEGF (Millipore™, rabbit 1/2000). The membranes were then washed 3 times with PBST. They were then treated with an appropriate horseradish peroxidase (HRP)-conjugated secondary antibody for 3 h at room temperature. The secondary antibodies were anti-rabbit IgG (P0448, DAKO™, Mississauga, Ontario, CA, 1/2,000) and anti-goat IgG (AP106P, Millipore™, Billerica, Ma, 1/3,000). The bands were visualized with an enhanced chemiluminescence system and exposure to photographic film (Hyperfilm ECL™, Amersham™ Pharmacia Biotech, Little Chalfont, UK). For reprobing of membranes with an alternative antibody, the membranes were treated with 10 mL of stripping buffer (3 mL of 1 M Tris-HCl pH 6.7, 10 mL of 10% SDS, 347 µL of 14 M mercaptoethanol, and 36.5 mL deionized water) at 60° C. for 1 h. The membrane was then placed on a shaking incubator for 30 min to clear it of all bound antibodies. The stripped membrane was then treated with a different primary antibody as previously described.

Experiment 3 was designed to determine if ATA, AQA, AHA and ATAC induced U251 cell apoptosis as revealed by DNA laddering. For determination of DNA laddering, which is indicative of DNA disintegration, cells were precipitated by centrifugation, washed, and lysed with 10 nM Tris-HCl, 5 mM EDTA, and 3% Triton-X-100. The lysates were incubated at 37° C. for 1 h and then centrifuged at 12,000g for 10 min. They were treated with phenol/chloroform/isoamylalcohol (25:24:1) and chloroform/isoamylalcohol (24:1) twice each, and precipitated with 0.6 volume isopropyl alcohol and 0.1 volume 3 M sodium actate at −20° C. for 30 min. The precipitates were centrifuged at 12,000 g for 20 min, washed with 70% ethanol and dissolved with TE buffer containing 2 µg/mL bovine RNase. DNAs were electrophoresed in 10 µg/mL ethidium bromide containing 2% w/v agarose gel.

Experiment 4 was designed to confirm apoptotic cell death of U251 cells induced by ATA, AQA, AHA, and ATAC by measuring release of lactic dehydrogenase into the cell medium. For serum lactate dehydrogenase determination, reaction supernatants (100 mL) were pipetted into the wells of 96-well plates, followed by the addition of 15 mL lactate solution (36 mg/mL in PBS) and 15 mL INT (iodonitrotetrazolium chloride, 2-(4-iodophenyl)-3-(4-nitrophenyl)-5-phenyl-2H-tetrazolium chloride) solution (2 mg/mL in PBS). The enzymatic reaction was started by addition of 15 mL of $NAD^+$/diaphorase solution (3 mg/mL $NAD^+$; 2.3 mg solid/mL diaphorase). After 1 h, optical densities were measured with a microplate reader using a 490 nm filter. The amount of LDH released was expressed as a percentage of the value obtained in comparative cells where cells were 100% lysed by 1% Triton X-100.

Figure 1B:
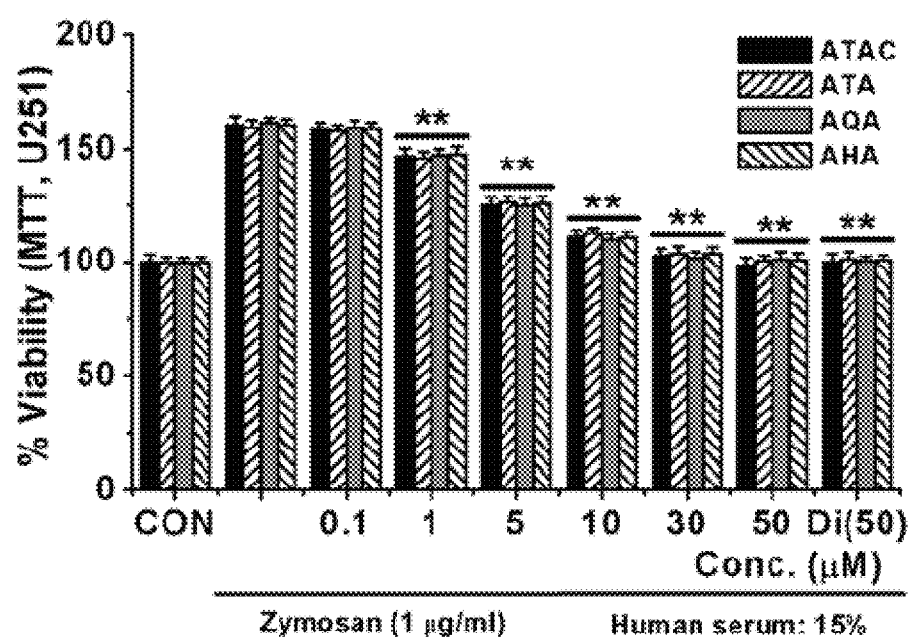
FIG. 1(b) is a graph plotting U251 cell viability as a function of the concentration of ATA, AQA, AHA and ATAC added to zymosan-activated human serum.

The results of Experiment 1 are illustrated in FIGS. 1(a) and 1(b), which each summarize data from four replicate experiments. The results of Experiment 1 demonstrate that ATAC, ATA, AQA and AHA inhibit U251 glioblastoma cell growth. FIG. 1(a) shows U251 cells increase their growth by zymosan-activated human serum complement. Values are mean±SEM, n=4. Significance of differences was tested by One-way ANOVA. $p<0.01$ for U251 cells grown in the media containing 7.5, 10, 12.5 and 15% human serum in the presence of 1 µg/ml zymosan compared with controls (10% human serum without zymosan). FIG. 1(b) shows ATAC, ATA, AQA, AHA inhibited U251 cell growth induced by zymosan-activated human serum complement in a concentration-dependent manner. Values are mean±SEM, n=4. Significance of differences was tested by One-way ANOVA. $p<0.01$ for ATA, AQA, AHA and ATAC-treated U251 cells (1-50 µM) compared with untreated human serum (15%) activated by zymosan. Di(50) group is the cells treated with ATA, AQA, AHA and ATAC (50 µM) and zymosan in the presence of heat inactivated serum. $IC_{50}$s for ATAC, ATA, AQA and AHA in µM are ATAC: 3.4, ATA: 3.5, AQA: 3.7 and AHA: 3.8, respectively. The data therefore establish that ATA, AQA, AHA and ATAC are equipotent in inhibiting growth of U251 cells. In the absence of these low molecular weight components of crude ATA, U251 cell growth increased as the concentration of zymosan-activated human serum was increased.

Figure 2:
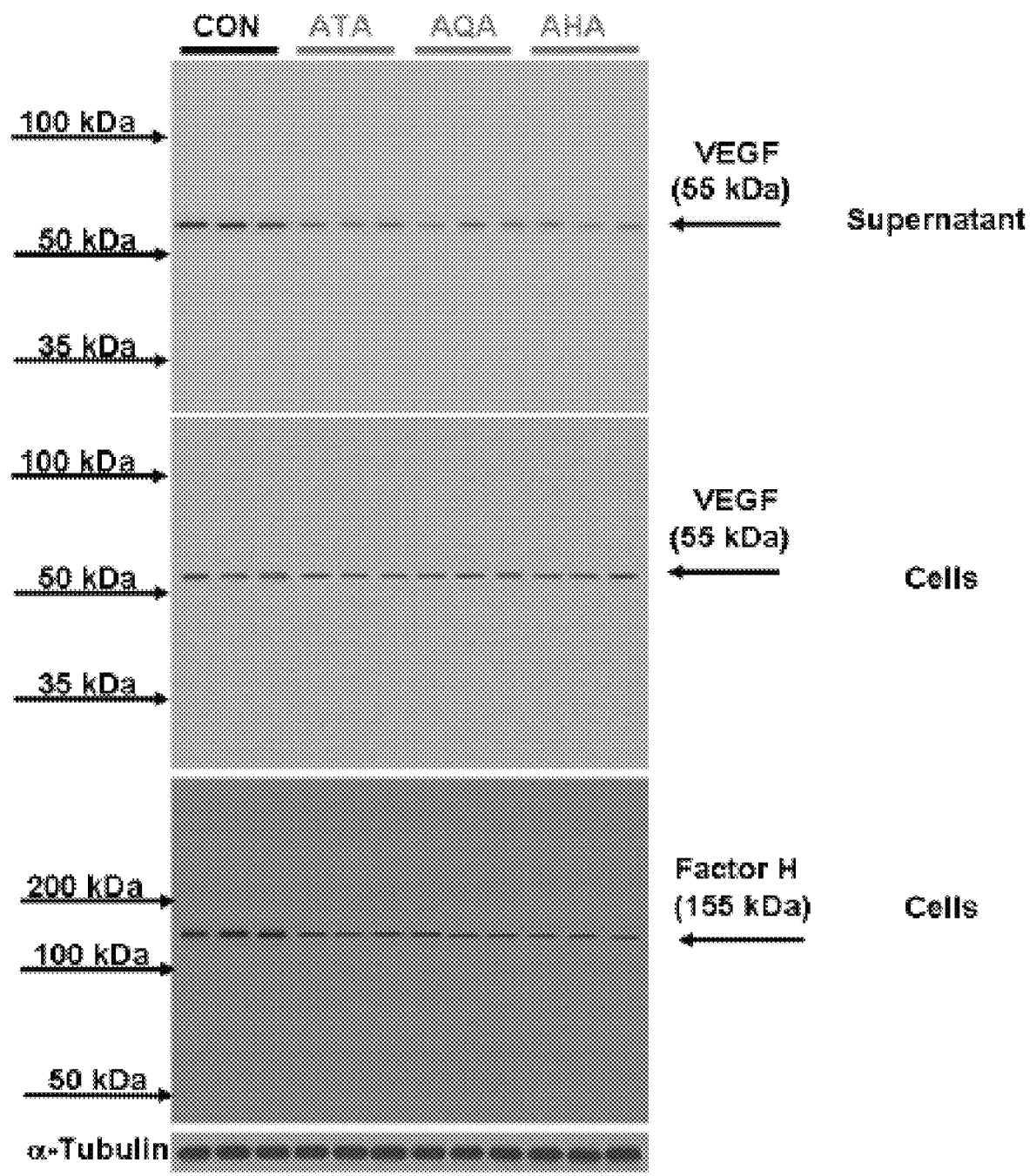
FIG. 2 is a western blot assay showing the effect of ATA, AHA and AQA on the expression and release of Factor H and VEGF by U251 cells.

The results of Experiment 2 are illustrated in FIG. 2. They show that ATA, AQA and AHA were relatively equipotent in reducing expression of vascular endothelial growth factor (VEGF, middle panel) and Factor H (bottom panel) in U251 cells. Cells ($10^8$) were treated with ATA, AQA and AHA (10 µM) each for 1 day and extracted for western blotting. Total of 100 µg protein was loaded. The two blots were from the same membrane. For reprobing with each antibody see protocol described above. For release of VEGF into the extracellular milieu, equal amounts of supernatant (1 mL) were collected to perform western blotting (top panel), with the results showing that ATA, AQA and AHA were relatively equipotent in reducing release of vascular endothelial growth factor as well. α-Tubulin was used as a loading control.

Figure 3:
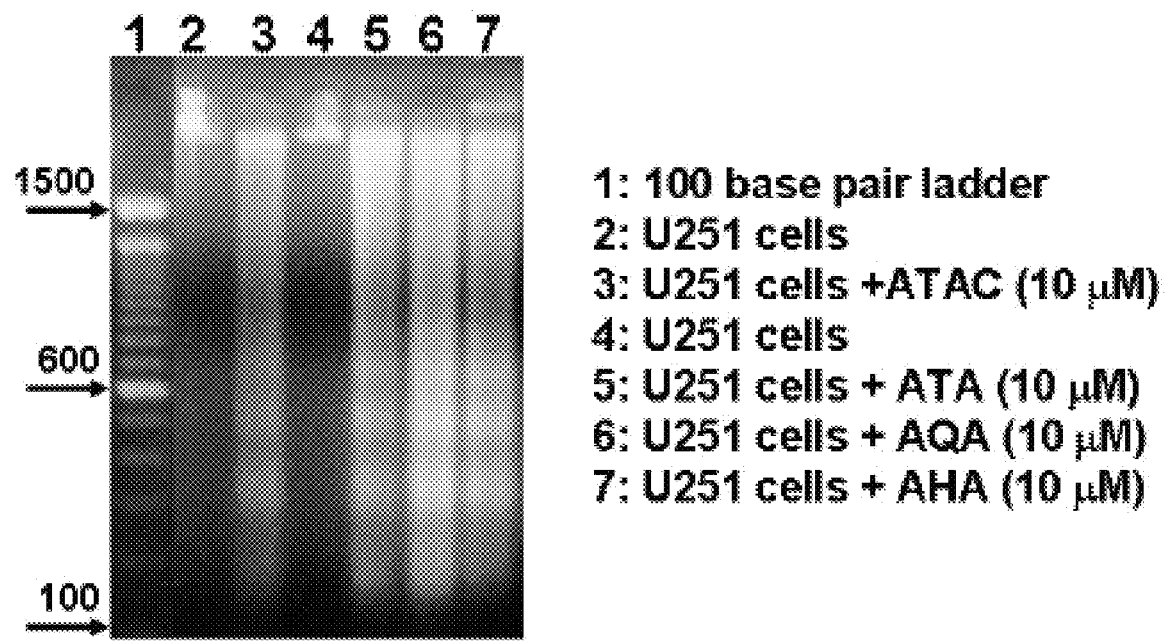
FIG. 3 is an agarose gel electrophoresis run showing the effect of ATA, AQA, AHA, and ATAC on DNA laddering of U251 cells.

The results of Experiment 3 are illustrated in FIG. 3. ATAC, ATA, AQA and AHA induced DNA fragmentation (180 bp laddering) in U251 cells. Cells ($10^8$) were treated with ATA, AQA and AHA (10 µM) each for 1 day and their supernatants (5 ml) were collected for DNA preparation as described above. There was no laddering from exposure to medium only.

Figure 4:
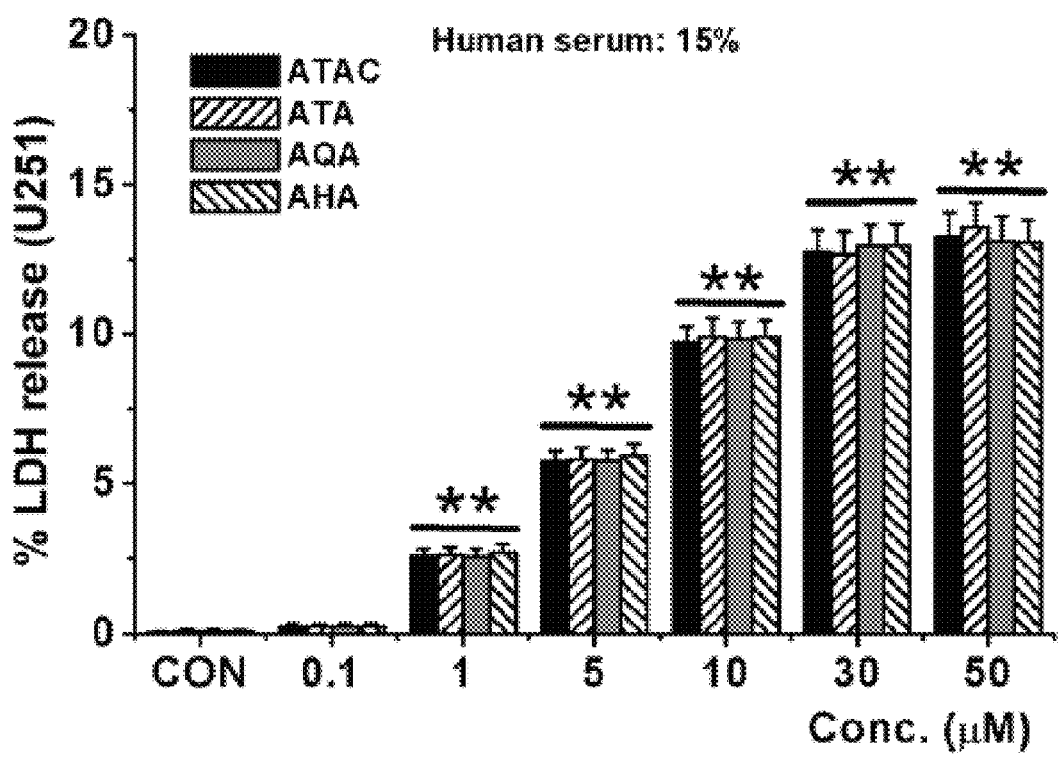
FIG. 4 is a graph plotting release of lactic dehydrogenase from U251 cells as a function of ATA, AQA, AHA and ATAC concentration.

The results of Experiment 4 are illustrated in FIG. 4. ATAC, ATA, AQA, and AHA induced lactate dehydrogenase release from U251 cells in a concentration-dependent manner. Values are mean±SEM, n=4. Significance of differences was tested by One-way ANOVA. **$p<0.01$ for ATA, AQA, AHA and ATAC-treated U251 cells (1-50 µM) compared with untreated cells. $IC_{50}$s for ATAC, ATA, AQA and AHA in µM are ATAC: 7.5, ATA: 7.6, AQA: 7.4 and AHA: 7.7, respectively. These data are consistent with apoptotic death as demonstrated in Experiment 3.

Example 2

Efficacy of ATA, AHA, AQA and ATAC against pancreatic cancer was tested using the BxPC-3 human pancreatic adenocarcinoma cell line. Serum and ATA, AQA, AHA, and ATAC were obtained as in Example 1.

Experiment 5 was designed to determine the effect of ATA, AHA, AQA and ATAC on BxPC-3 cell growth in the presence of complement activated human serum. The protocol was comparable to Experiment 1 except that the growth medium was RPMI 1640.

Experiment 6 was designed to determine the effect of ATA, AQA, and AHA on the expression and release of Factor H and VEGF by BxPC-3 cells. The protocol was comparable to Experiment 2 except that the growth medium was RPMI 1640.

Experiment 7 was designed to determine if ATA, AQA, AHA and ATAC affected BxPC-3 cell apoptosis as revealed by DNA laddering. The protocol was comparable to Experiment 3 except that the growth medium was RPMI 1640.

Experiment 8 was designed to confirm apoptotic cell death of BxPC-3 cells induced by ATA, AQA, AHA, and ATAC by the release of lactic dehydrogenase into the cell medium. The protocol was comparable to Experiment 4 except that the growth medium was RPMI 1640.

Figure 5A:
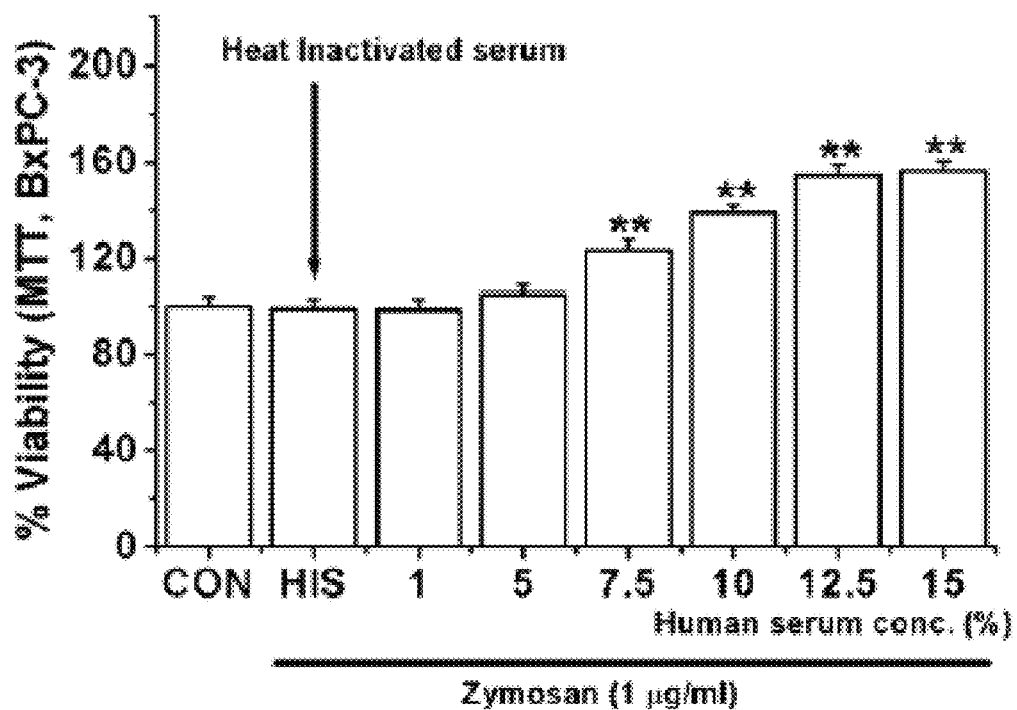
FIG. 5(a) is a graph plotting BxPC-3 human pancreatic adenocarcinoma cell viability as a function of zymosan-activated human serum concentration.
Figure 5B:
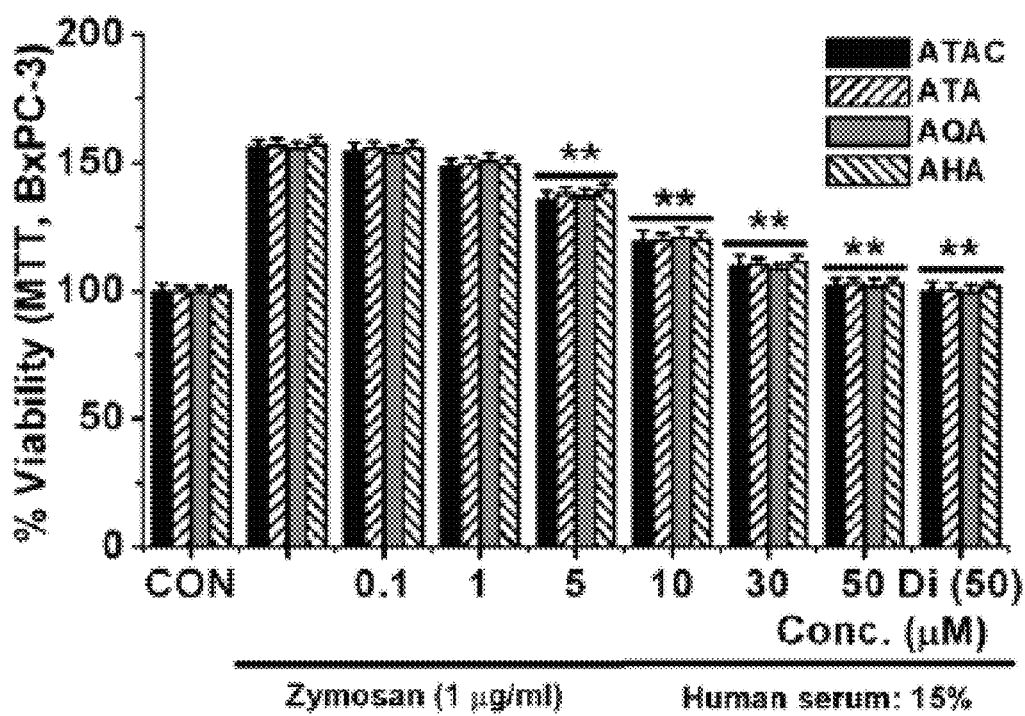
FIG. 5(b) is a graph plotting BxPC-3 cell viability as a function of the concentration of ATA, AQA, AHA and ATAC added to zymosan-activated human serum.

The results of Experiment 5 are illustrated in FIGS. 5(a) and 5(b), which each summarize data from four replicate experiments. The results of Experiment 5 demonstrate that ATAC, ATA, AQA and AHA inhibited BxPC-3 cell growth. FIG. 5(a) shows BxPC-3 cells increase their growth by zymosan-activated human serum complement. Values are mean±SEM, n=4. Significance of differences was tested by One-way ANOVA. $p<0.01$ for U251 cells grown in the media containing 7.5, 10, 12.5 and 15% human serum in the presence of 1 µg/ml zymosan compared with controls (10% human serum without zymosan). FIG. 5(b) shows ATAC, ATA, AQA, AHA inhibited U251 cell growth induced by zymosan-activated human serum complement in a concentration-dependent manner. Values are mean±SEM, n=4. Significance of differences was tested by One-way ANOVA. $p<0.01$ for ATA, AQA, AHA and ATAC-treated U251 cells (1-50 µM) compared with untreated human serum (15%) activated by zymosan. Di(50) group is the cells treated with ATA, AQA, AHA and ATAC (50 μM) and zymosan in the presence of heat inactivated serum. $IC_{50}s$ for ATAC, ATA, AQA and AHA in μM are ATAC: 6.4, ATA: 6.5, AQA: 6.7 and AHA: 6.8, respectively. The data establish that ATA, AQA, AHA and ATAC are equipotent in inhibiting growth of BxPC-3 cells. In the absence of these low molecular weight components of crude ATA, BxPC-3 cell growth increased as the concentration of zymosan-activated human serum was increased.

Figure 6:
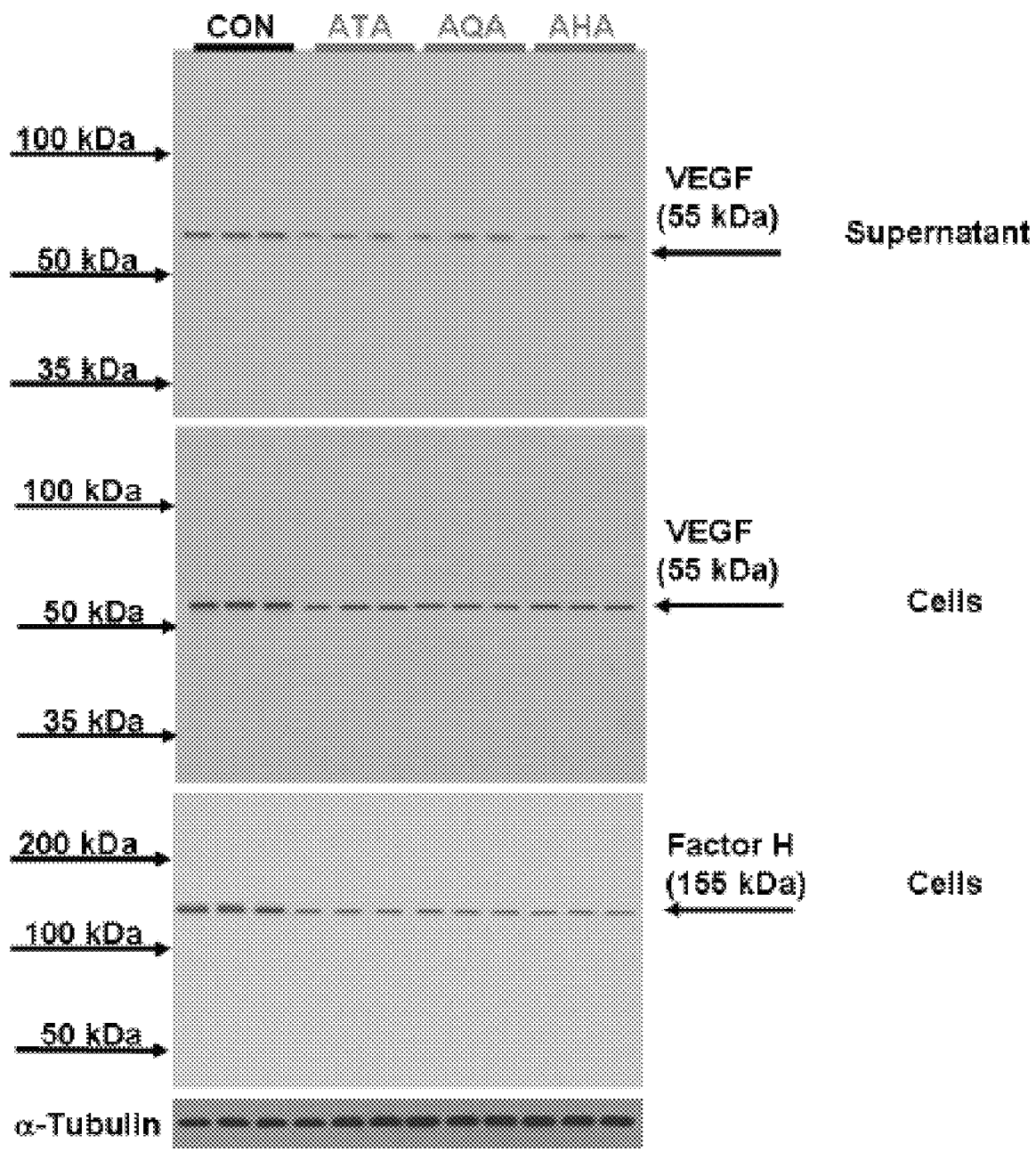
FIG. 6 is a western blot assay showing the effect of ATA, AQA and AHA on the expression and release of Factor H and VEGF by BxPC-3 cells.

The results of Experiment 6 are illustrated in FIG. 6. They establish by western blotting that ATA, AQA and AHA were relatively equipotent in reducing expression of vascular endothelial growth factor (VEGF, middle panel) and Factor H (bottom panel) in BxPC-3 cells. Cells ($10^8$) were treated with ATA, AQA and AHA (10 μM) each for 1 day and extracted for western blotting. Total of 100 μg protein was loaded. The two blots were from the same membrane. For reprobing with each antibody see protocol described above. For release of VEGF into the extracellular milieu, equal amounts of supernatant (1 mL) were collected to perform western blotting (top panel), with the results showing that ATA, AQA and AHA were relatively equipotent in reducing release of vascular endothelial growth factor as well. α-Tubulin was used as a loading control.

Figure 7:
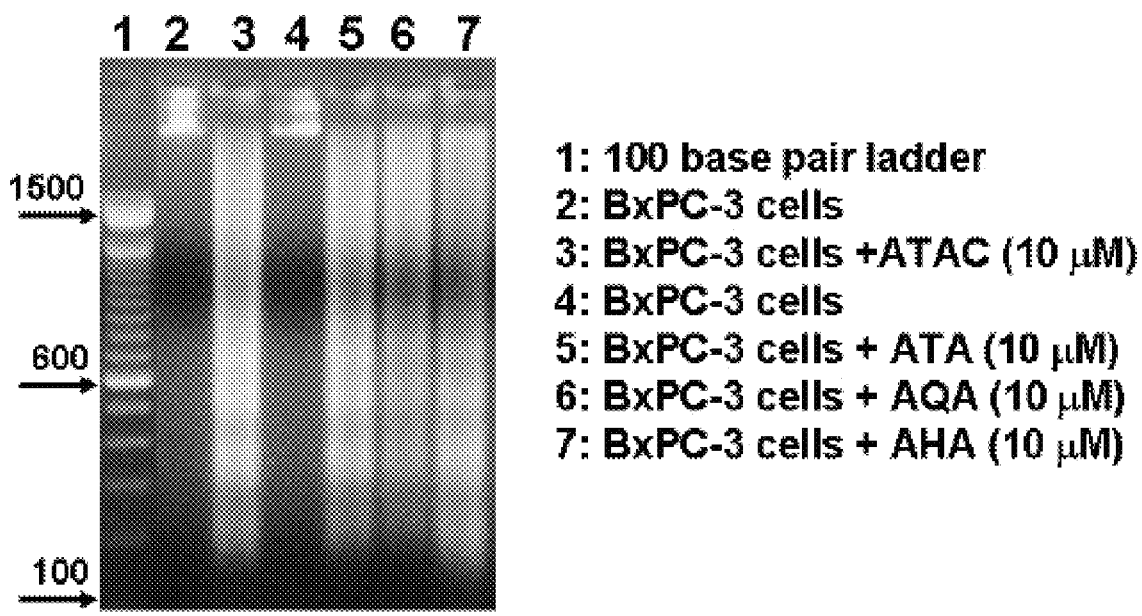
FIG. 7 is an agarose gel electrophoresis run showing the effect of ATA, AQA, AHA, and ATAC on DNA laddering of BxPC-3 cells.

The results of Experiment 7 are illustrated in FIG. 7. They show induction of DNA laddering, indicative of apoptosis, in BxPC-3 cells. ATAC, ATA, AQA and AHA induced DNA fragmentation (180 bp laddering) in BxPC-3 cells. Cells ($10^8$) were treated with ATA, AQA and AHA (10 μM) each for 1 day and their supernatants (5 ml) were collected for DNA preparation as described above. There was no laddering from exposure to medium only.

Figure 8:
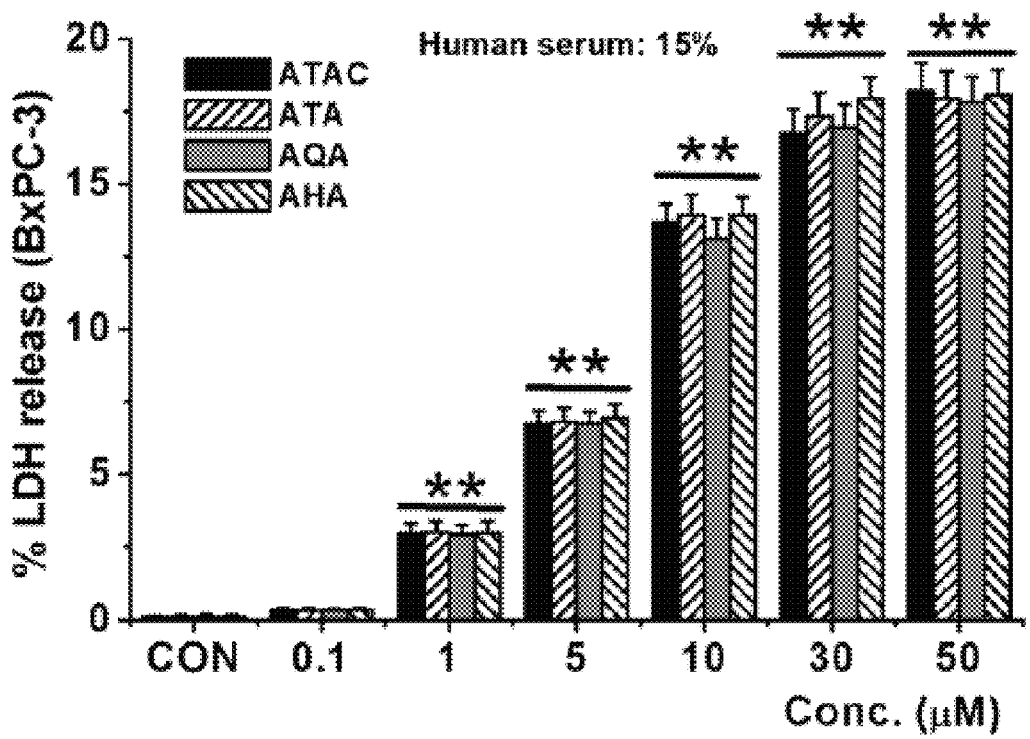
FIG. 8 is a graph plotting release of lactic dehydrogenase from BxPC-3 cells as a function of ATA, AQA, AHA and ATAC concentration.

The results of Experiment 8 are illustrated in FIG. 8. They show substantial release of lactic dehydrogenase (LDH) into the culture medium of cells following exposure to ATA, AQA, AHA, or ATAC but no release following exposure to medium only. ATAC, ATA, AQA, and AHA induced lactate dehydrogenase release from BxPC-3 cells in a concentration-dependent manner. Values are mean±SEM, n=4. Significance of differences was tested by One-way ANOVA. **$p<0.01$ for ATA, AQA, AHA, and ATAC-treated U251 cells (1-50 μM) compared with untreated cells. $IC_{50}s$ for ATAC, ATA, AQA and AHA in μM are ATAC: 7.8, ATA: 7.9, AQA: 8.0 and AHA: 8.1, respectively. These data are consistent with apoptotic death as demonstrated in Experiment 7.

Example 3

Efficacy of ATA, AHA, AQA and ATAC against lung cancer was tested using the A549 human lung cancer cell line. ATA, AQA, AHA and ATAC were obtained as in Example 1.

Experiment 9 was designed to determine the effect of ATA, AQA, AHA and ATAC on A549 cell growth. The protocol was identical to that used in Experiment 5(b) except A549 cells were used.

Experiment 10 was designed to determine the effect of ATA, AQA, and AHA on the expression and release of Factor H and VEGF by A549 cells. The protocol was identical to that used in Experiment 6 except A549 cells were used.

Experiment 11 was designed to determine if ATA, AQA, AHA and ATAC affected A549 cell apoptosis as revealed by DNA laddering. The protocol was identical to that used in Experiment 7 except A549 cells were used.

Experiment 12 was designed to confirm apoptotic cell death of A549 cells induced by ATA, AQA, AHA, and ATAC by the release of lactic dehydrogenase into the cell medium. The protocol was identical to that used in Experiment 8 except A549 cells were used.

Figure 9:
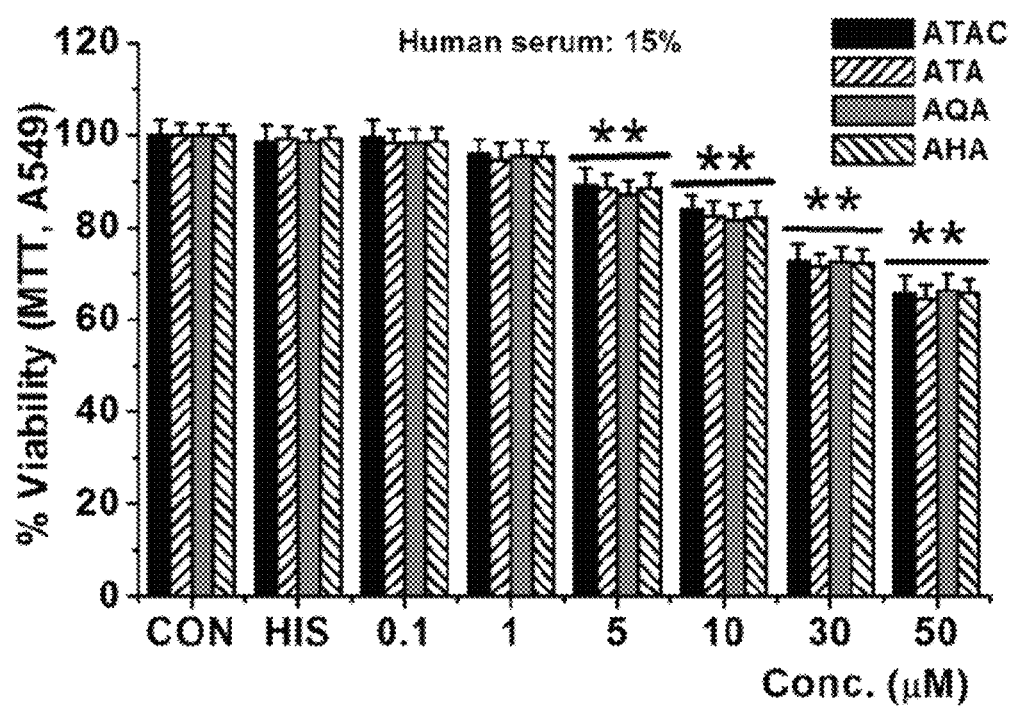
FIG. 9 is a graph plotting A549 lung carcinoma cell viability as a function of the concentration of ATA, AQA, AHA and ATAC added to zymosan-activated human serum.

The results of Experiment 9 are shown in FIG. 9. ATAC, ATA, AQA and AHA inhibited A549 cell growth induced by zymosan-activated human serum complement in a concentration-dependent manner. Values are mean±SEM, n=4. Significance of differences was tested by One-way ANOVA. **$p<0.01$ for ATAC, ATA, AQA and AHA-treated A549 cells (5-50 μM) compared with untreated human serum (15%) activated by zymosan. $IC_{50}s$ for ATAC, ATA, AQA and AHA in μM are ATAC: 7.3, ATA: 7.2, AQA: 7.4 and AHA: 7.5, respectively.

Figure 10:
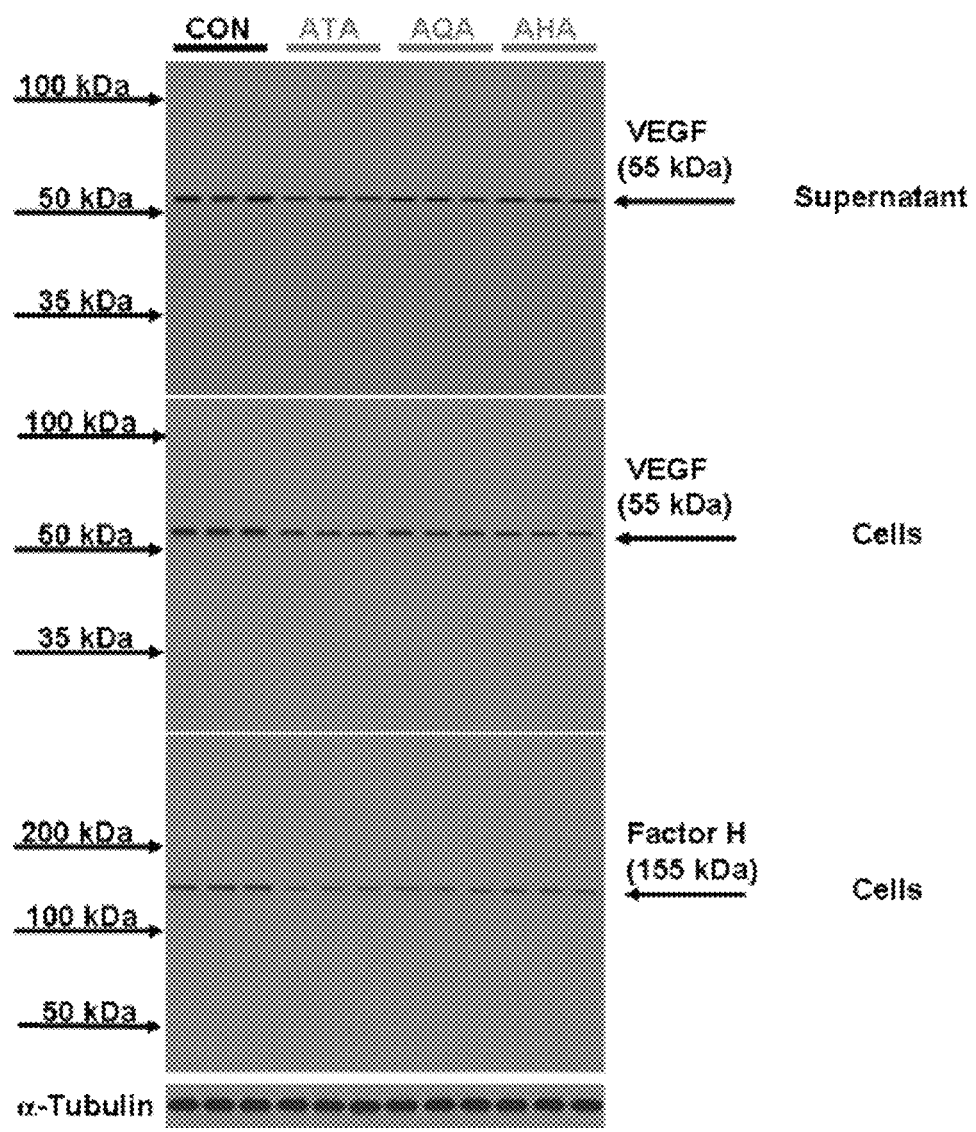
FIG. 10 is a western blot assay showing the effect of ATA, AQA and AHA on the expression and release of Factor H and VEGF by A549 cells.

The results of Experiment 10 are illustrated in FIG. 10. ATA, AQA and AHA reduced expression of vascular endothelial growth factor (VEGF, middle panel) and Factor H (bottom panel) in A549 cells. Cells ($10^8$) were treated with ATA, AQA and AHA (10 μM) each for 1 day and extracted for western blotting. Total of 100 μg protein was loaded. The two blots were from the same membrane. For reprobing with each antibody see protocol described above. For release of VEGF into the extracellular milieu, equal amounts of supernatant (1 mL) were collected to perform western blotting (top panel), with the results showing that ATA, AQA and AHA were relatively equipotent in reducing release of vascular endothelial growth factor as well. α-Tubulin was used as a loading control.

Figure 11:
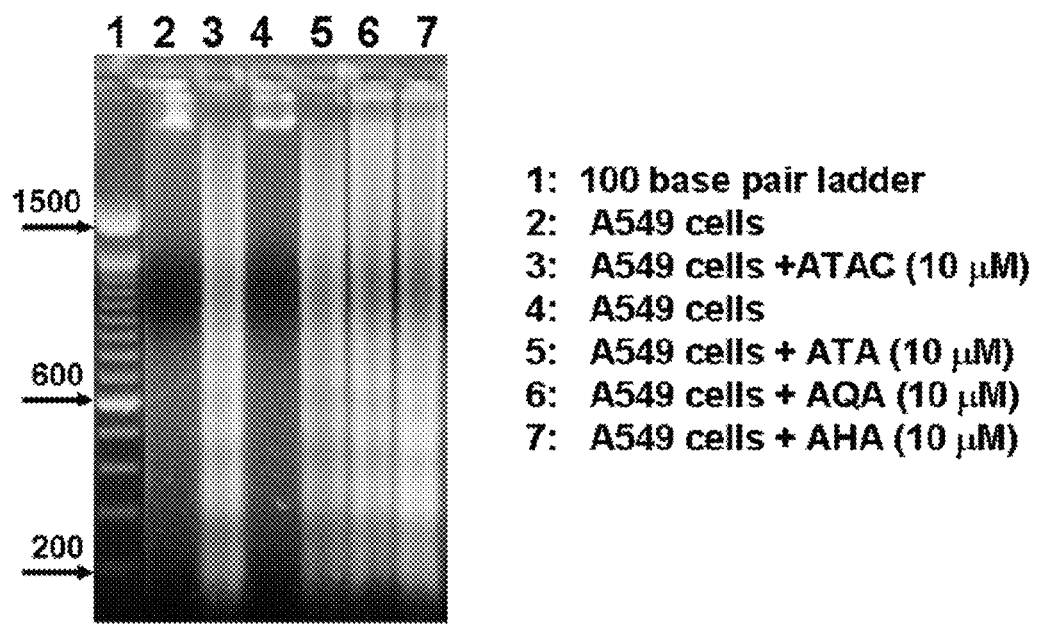
FIG. 11 is an agarose gel electrophoresis run showing the effect of ATA, AQA, AHA, and ATAC on DNA laddering of A549 cells.

The results of Experiment 11 are illustrated in FIG. 11. ATAC, ATA, AQA and AHA induced DNA fragmentation (180 bp laddering) in A549 cells. Cells ($10^8$) were treated with ATA, AQA and AHA (10 μM) each for 1 day and their supernatants (5 ml) were collected for DNA preparation as described above. There was no laddering from exposure to medium only.

Figure 12:
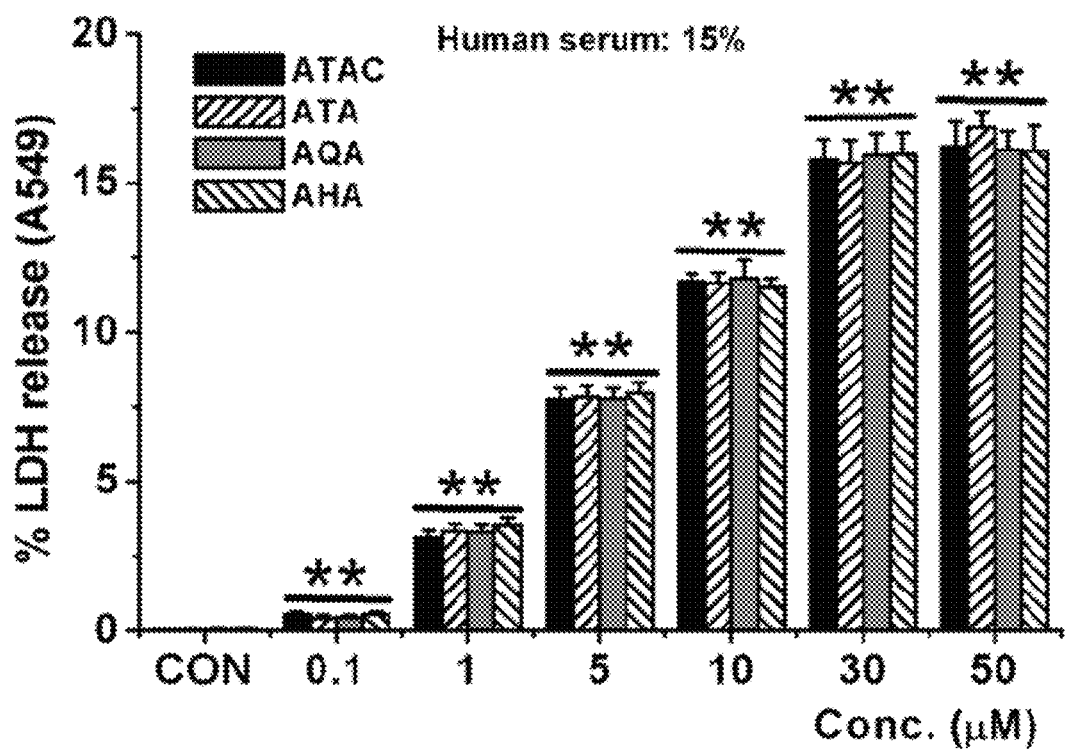
FIG. 12 is a graph plotting release of lactic dehydrogenase from A549 cells as a function of ATA, AQA, AHA and ATAC concentration.

The results of Experiment 12 are illustrated in FIG. 12. ATAC, ATA, AQA, and AHA induced lactate dehydrogenase release from A549 cells in a concentration-dependent manner. Values are mean±SEM, n=4. Significance of differences was tested by One-way ANOVA. **$p<0.01$ for ATAC, ATA, AQA, and AHA-treated U251 cells (1-50 μM) compared with untreated cells. $IC_{50}s$ for ATAC, ATA, AQA and AHA in μM are ATAC: 7.3, ATA: 7.5, AQA: 7.4 and AHA: 7.6, respectively.

Example 4

Efficacy of ATA, AHA, AQA and ATAC against breast cancer was tested using the BT 474 human breast cancer cell line. ATA, AQA, AHA and ATAC were obtained as in Example 1.

Experiment 13 was designed to determine the effect of ATA, AQA, AHA and ATAC on BT 474 cell growth. The protocol was identical to that used in Experiment 1(b) except BT 474 cells were used.

Experiment 14 was designed to determine if apoptotic cell death of BT 474 cells was induced by ATA, AQA, AHA, and ATAC as determined by the release of lactic dehydrogenase into the cell medium. The protocol was identical to that used in Experiment 5(d) except that BT 474 cells were used.

Figure 13A:
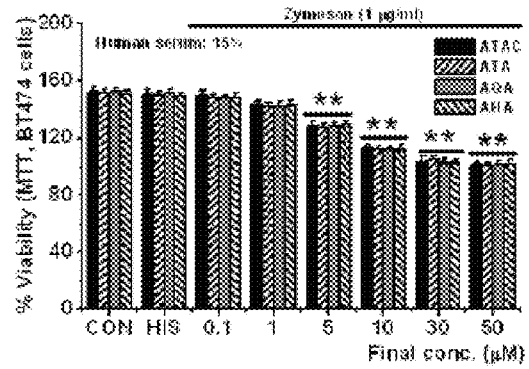
FIGS. 13(a) to (f) are graphs plotting inhibition of zymosan-activated human serum complement induced cell growth of (a) BT474 breast carcinoma cells, (b) DOHH2 B cell carcinoma cells, (c) K562 chronic myelogenic leukemia cells, (d) LS180 colorectal adenocarcinoma cells, (e) MNNG bone osteocarcinoma cells and (f) SW480 colorectal adenocarcinoma cells, as a function of ATA, AQA, AHA and ATAC concentration.
Figure 14A:
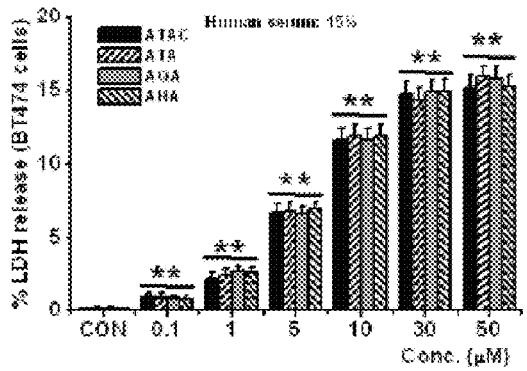
FIG. 14(a) to (f) are graphs plotting release of lactic dehydrogenase from (a) BT474 breast carcinoma cells, (b) DOHH2 B cell carcinoma cells, (c) K562 chronic myelogenic leukemia cells, (d) LS180 colorectal adenocarcinoma cells, (e) MNNG bone osteocarcinoma cells and (f) SW480 colorectal adenocarcinoma cells, as a function of ATA, AQA, AHA and ATAC concentration.

The results of Experiment 13 are shown in FIG. 13(a). ATAC, ATA, AQA and AHA inhibited B474 cell growth induced by zymosan-activated human serum complement in a concentration-dependent manner. Values are mean±SEM, n=4. Significance of differences was tested by One-way ANOVA. $p<0.01$ for ATAC, ATA, AQA and AHA-treated cells compared with untreated cells in human serum (15%) activated by zymosan. IC50s in μM are ATAC: 5.7, ATA: 5.9, AQA: 6.0 and AHA: 5.8, respectively. The results of Experiment 14 are illustrated in FIG. 14(a). ATAC, ATA, AQA, and AHA induced lactate dehydrogenase release from BT 474 cells in a concentration-dependent manner. Values are mean±SEM, n=4. Significance of differences was tested by One-way ANOVA. p<0.01 for ATAC, ATA, AQA, and AHA-treated BT 474 cells (1-50 μM) compared with untreated cells. $IC_{50}$s for ATAC, ATA, AQA and AHA in μM are ATAC: 4.7, ATA: 4.8, AQA: 4.7 and AHA: 4.9, respectively.

Example 5

Efficacy of ATA, AHA, AQA and ATAC against B-cell carcinoma was tested using the DOHH2 human B-cell carcinoma cell line. ATA, AQA, AHA and ATAC were obtained as in Example 1.

Experiment 15 was designed to determine the effect of ATA, AQA, 15 AHA and ATAC on DOHH2 human B-cell carcinoma cell growth. The protocol was identical to that used in Experiment 9(b) except DOHH2 human B-cell carcinoma cells were used.

Experiment 16 was designed to determine if apoptotic cell death of DOHH2 human B-cell carcinoma cells was induced by ATA, AQA, AHA, and ATAC as determined by the release of lactic dehydrogenase into the cell medium. The protocol was identical to that used in Experiment 9(d) except that DOHH2 human B-cell carcinoma cells were used.

Figure 13B:
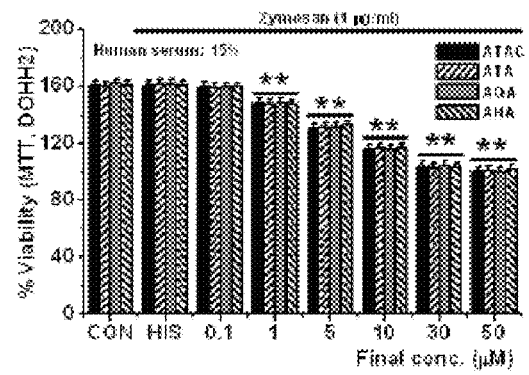

The results of Experiment 15 are shown in FIG. 13(b). ATAC, ATA, AQA and AHA inhibited DOHH2 human B-cell carcinoma cell growth induced by zymosan-activated human serum complement in a concentration-dependent manner. Values are mean±SEM, n=4. Significance of differences was tested by One-way ANOVA. **p<0.01 for ATAC, ATA, AQA and AHA-treated DOHH2 human B-cell carcinoma cells compared with untreated human serum (15%) activated by zymosan. $IC_{50}$s for ATAC, ATA, AQA and AHA in μM are ATAC: 4.9, ATA: 5.1, AQA: 5.0 and AHA: 4.9, respectively.

Figure 14B:
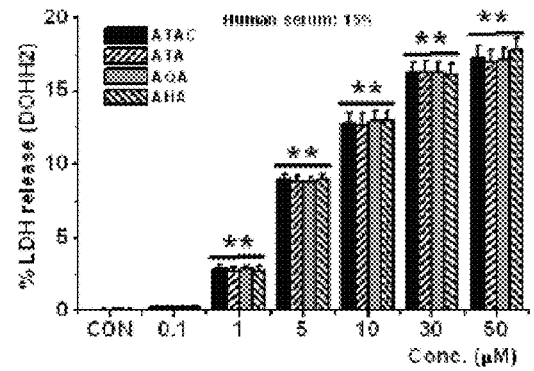

The results of Experiment 16 are illustrated in FIG. 14(b). ATAC, ATA, AQA, and AHA induced lactate dehydrogenase release from DOHH2 human B-cell carcinoma cells in a concentration-dependent manner. Values are mean±SEM, n=4. Significance of differences was tested by One-way ANOVA. **p<0.01 for ATAC, ATA, AQA, and AHA-treated DOHH2 human B-cell carcinoma cells compared with untreated cells. $IC_{50}$s for ATAC, ATA, AQA and AHA in μM are ATAC: 5.0, ATA: 4.9, AQA: 5.0 and AHA: 5.1, respectively.

Example 6

Efficacy of ATA, AHA, AQA and ATAC against chronic myelogenous leukemia was tested using the K562 human chronic myelogenous leukemia cell line. ATA, AQA, AHA and ATAC were obtained as in Example 1.

Experiment 17 was designed to determine the effect of ATA, AQA, AHA and ATAC on K562 human chronic myelogenous leukemia cell growth. The protocol was identical to that used in Experiment 15(b) except that K562 human chronic myelogenous were utilized and the growth medium was Iscove's.

Experiment 18 was designed to determine if apoptotic cell death of K562 human chronic myelogenous leukemia cells was induced by ATA, AQA, AHA, and ATAC as determined by the release of lactic dehydrogenase into the cell medium. The protocol was identical to that used in Experiment 16(b) except that K562 human chronic myelogenous leukemia cells were used.

Figure 13C:
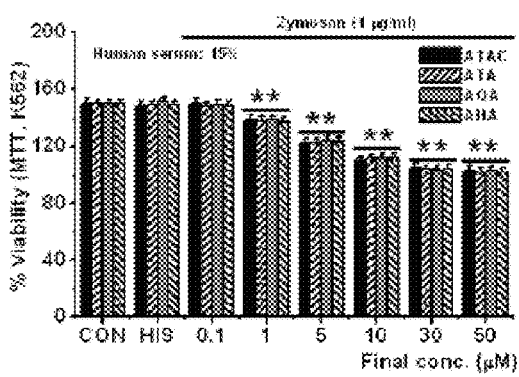

The results of Experiment 17 are shown in FIG. 13(c). ATAC, ATA, AQA and AHA inhibited DOHH2 human B-cell carcinoma cell growth induced by zymosan-activated human serum complement in a concentration-dependent manner. Values are mean±SEM, n=4. Significance of differences was tested by One-way ANOVA. **p<0.01 for ATAC, ATA, AQA and AHA-treated K562 human chronic myelogenous leukemia cells compared with untreated human serum (15%) activated by zymosan. $IC_{50}$s for ATAC, ATA, AQA and AHA in μM are ATAC: 4.6, ATA: 4.5, AQA: 4.7 and AHA: 4.6, respectively.

Figure 14C:
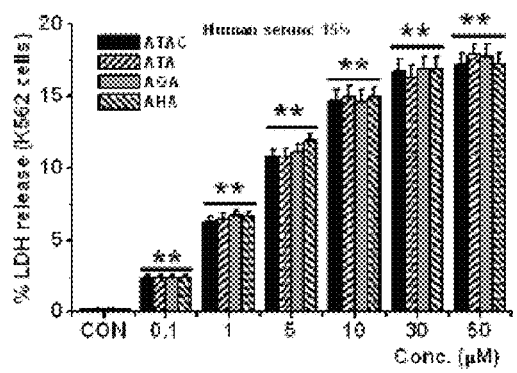

The results of Experiment 18 are illustrated in FIG. 14(c). ATAC, ATA, AQA, and AHA induced lactate dehydrogenase release from K562 human chronic myelogenous leukemia cells DOHH2 in a concentration-dependent manner. Values are mean±SEM, n=4. Significance of differences was tested by One-way ANOVA. **p<0.01 for ATAC, ATA, AQA, and AHA-treated K562 human chronic myelogenous leukemia cells compared with untreated cells. $IC_{50}$s for ATAC, ATA, AQA and AHA in μM are ATAC: 4.5, ATA: 4.7, AQA: 4.6 and AHA: 4.6, respectively.

Example 7

Efficacy of ATA, AHA, AQA and ATAC against colorectal adenocarcinoma was tested using the human colorectal adenocarcinoma cell line LS180. ATA, AQA, AHA and ATAC were obtained as in Example 1.

Experiment 19 was designed to determine the effect of ATA, AQA, AHA and ATAC on growth of the human colorectal adenocarcinoma LS180 cell line. The protocol was identical to that used in Experiment 17(b) except that colorectal adenocarcinoma cells were utilized and the growth medium was EMEM.

Experiment 20 was designed to determine if apoptotic death of colorectal adenocarcinoma LS180 cells was induced by ATA, AQA, AHA, and ATAC as determined by the release of lactic dehydrogenase into the cell medium. The protocol was identical to that used in Experiment 18(b) except that colorectal adenocarcinoma cells were used.

Figure 13D:
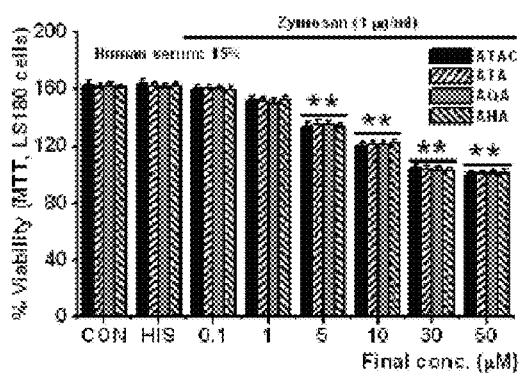

The results of Experiment 19 are shown in FIG. 13(d). ATAC, ATA, AQA and AHA inhibited growth of LS180 colorectal adenocarcinoma cells induced by zymosan-activated human serum complement in a concentration-dependent manner. Values are mean±SEM, n=4. Significance of differences was tested by One-way ANOVA. **p<0.01 for ATAC, ATA, AQA and AHA-treated colorectal adenocarcinoma LS 180 cells compared with untreated human serum (15%) activated by zymosan. $IC_{50}$s for ATAC, ATA, AQA and AHA in μM are ATAC: 4.9, ATA: 4.8, AQA: 5.2 and AHA: 5.1, respectively.

Figure 14D:
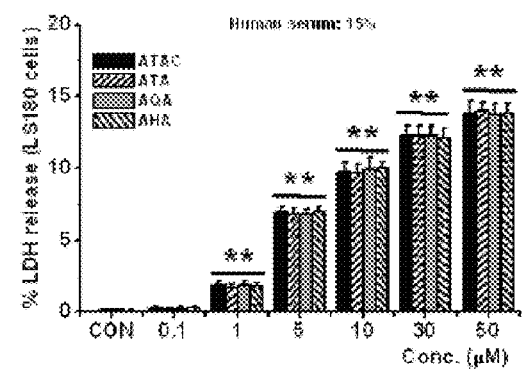

The results of Experiment 20 are illustrated in FIG. 14(d). ATAC, ATA, AQA, and AHA induced lactate dehydrogenase release from colorectal adenocarcinoma LS180 cells in a concentration-dependent manner. Values are mean±SEM, n=4. Significance of differences was tested by One-way ANOVA. **p<0.01 for ATAC, ATA, AQA, and AHA-treated colorectal adenocarcinoma LS180 cells compared with untreated cells. $IC_{50}$s for ATAC, ATA, AQA and AHA in μM are ATAC: 4.8, ATA: 4.9, AQA: 5.1 and AHA: 5.0, respectively.

Example 8

Efficacy of ATA, AHA, AQA and ATAC against bone osteosarcoma was tested using the human bone osteosarcoma MNNG cells. ATA, AQA, AHA and ATAC were obtained as in Example 1.

Experiment 21 was designed to determine the effect of ATA, AQA, AHA and ATAC on growth of the human bone osteosarcoma MNNG cell line. The protocol was identical to that used in Experiment 19 (b) except that human bone osteosarcoma MNNG cells were utilized.

Experiment 22 was designed to determine if apoptotic death of human bone osteosarcoma MNNG cells was induced by ATA, AQA, AHA, and ATAC as determined by the release of lactic dehydrogenase into the cell medium. The protocol was identical to that used in Experiment 19(d) except that human bone osteosarcoma MNNG cells were used.

Figure 13E:
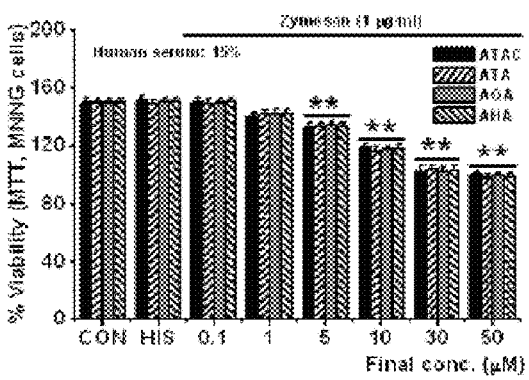

The results of Experiment 21 are shown in FIG. 13(e). ATAC, ATA, AQA and AHA inhibited growth of human bone osteosarcoma MNNG cells induced by zymosan-activated human serum complement in a concentration-dependent manner. Values are mean±SEM, n=4. Significance of differences was tested by One-way ANOVA. **p<0.01 for ATAC, ATA, AQA and AHA-treated human bone osteosarcoma MNNG cells compared with untreated human serum (15%) activated by zymosan. $IC_{50}$s for ATAC, ATA, AQA and AHA in µM are ATAC: 7.3, ATA: 7.2, AQA: 7.4 and AHA: 7.5, respectively.

Figure 14E:
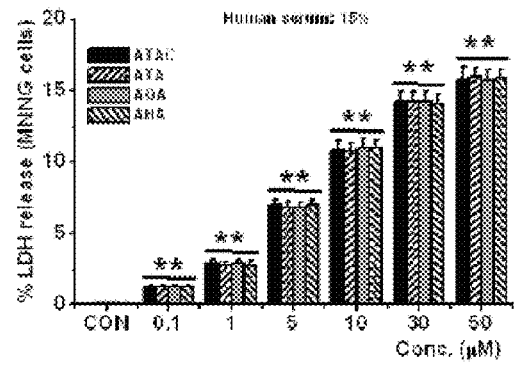

The results of Experiment 22 are illustrated in FIG. 14(e). ATAC, ATA, AQA, and AHA induced lactate dehydrogenase release from human bone osteosarcoma MNNG cells in a concentration-dependent manner. Values are mean±SEM, n=4. Significance of differences was tested by One-way ANOVA. **p<0.01 for ATAC, ATA, AQA, and AHA-treated human bone osteosarcoma MNNG cells compared with untreated cells. $IC_{50}$s for ATAC, ATA, AQA and AHA in µM are ATAC: 6.3, ATA: 6.5, AQA: 6.4 and AHA: 6.6, 10 respectively.

Example 9

Efficacy of ATA, AHA, AQA and ATAC against colorectal cancer cells was tested using the human colorectal cancer cell line SW 480. AQA, AHA and ATAC were obtained as in Example 1.

Experiment 23 was designed to determine the effect of ATA, AQA, 15 AHA and ATAC on growth of the human colorectal cancer cell line SW 480. The protocol was identical to that used in Experiment 15(b) except that human colorectal cancer SW480 cells were utilized. Experiment 24 was designed to determine if apoptotic death of human carcinoma SW 480 cells was induced by ATA, AQA, AHA, and ATAC as determined by the release of lactic dehydrogenase into the cell medium. The protocol was identical to that used in Experiment 15(d) except that human carcinoma SW480 cells were used and the growth medium was DMEM.

Figure 13F:
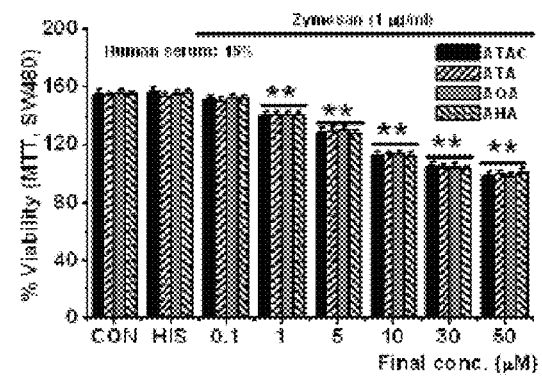

The results of Experiment 23 are shown in FIG. 13(f). ATAC, ATA, AQA and AHA inhibited growth of human carcinoma SW 480 cells induced by zymosan-activated human serum complement in a concentration-dependent manner.

Values are mean±SEM, n=4. Significance of differences was tested by One-way ANOVA. **p<0.01 for ATAC, ATA, AQA and AHA-treated human carcinoma SW 480 cells compared with untreated human serum (15%) activated by zymosan. $IC_{50}$s for ATAC, ATA, AQA and AHA in µM are ATAC: 6.9, ATA: 7.0, AQA: 7.0 and AHA: 6.8, respectively.

Figure 14F:
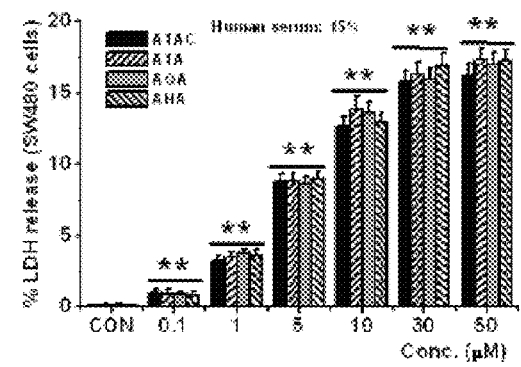

The results of Experiment 24 are illustrated in FIG. 14(f). ATAC, ATA, AQA, and AHA induced lactate dehydrogenase release from human carcinoma SW 480 cells in a concentration-dependent manner. Values are mean±SEM, n=4. Significance of differences was tested by One-way ANOVA. **p<0.01 for ATAC, ATA, AQA, and AHA-treated human carcinoma SW480 cells compared with untreated cells. $IC_{50}$s for ATAC, ATA, AQA and AHA in µM are ATAC: 4.9, ATA: 4.7, AQA: 4.6 and AHA: 4.9, 10 respectively.

CONCLUSION

As those skilled in the art will appreciate, the methods and uses described herein are only examples of many conditions where the invention may be applied to produce prophylactic and/or therapeutic benefit. Specific pharmacological responses observed may vary according to and depending on the particular active agent(s) and/or pharmaceutical acceptable carrier(s) selected, as well as the type of formulation and mode of administration employed, and such expected variations or differences in the results are contemplated in accordance with practice of the present invention.

This application is intended to cover any variations, uses, or adaptations of the invention using its general principles. Further, this application is intended to cover such departures from the present disclosure as come within known or customary practice in the art to which this invention pertains and which fall within the limits of the appended claims. Accordingly, the scope of the claims should not be limited by the preferred embodiments set forth in the description, but should be given the broadest interpretation consistent with the description as a whole.

What is claimed is:

1. A kit comprising an active agent selected from the group consisting of ATA, AQA, AHA, ATAC, and a pharmaceutically acceptable salt thereof, and a package insert comprising instructions for using the active agent to treat cancer in a subject, wherein the active agent excludes any components greater than or equal to 1 kilodalton in molecular weight, wherein the ATA is purified ATA, the AQA is purified AQA, and the AHA is purified AHA, and wherein the cancer is selected from the group consisting of ovarian cancer, breast cancer, B-cell carcinoma, colorectal adenocarcinoma, colorectal cancer, chronic myelogenous leukemia, bone osteosarcoma glioblastoma, pancreatic cancer, and lung cancer.

2. A kit according to claim 1 wherein the active agent is the purified ATA.

3. A kit according to claim 1 wherein the active agent is the purified AQA.

4. A kit according to claim 1 wherein the active agent is the purified AHA.

5. A kit according to claim 1 wherein the active agent is the purified ATAC.

6. A kit according to claim 5 wherein the ATAC comprises a mixture of two or more of ATA, AQA and AHA.

7. A kit according to claim 5 wherein the ATAC comprises 50 to 90% ATA, 10 to 30% AQA, and 1 to 20% AHA.

* * * * *